(12) United States Patent
Debetencourt

(10) Patent No.: US 8,597,696 B2
(45) Date of Patent: Dec. 3, 2013

(54) PHARMACEUTICAL COMPOSITION FOR TREATING CUTANEOUS BURNS

(75) Inventor: Jean-Jacques Debetencourt, Walmer (GB)

(73) Assignee: 45 Sec. LLC, Lewes, DE (US)

( * ) Notice: Subject to any disclaimer, the term of this patent is extended or adjusted under 35 U.S.C. 154(b) by 0 days.

(21) Appl. No.: 13/514,625

(22) PCT Filed: Dec. 10, 2010

(86) PCT No.: PCT/EP2010/069412
§ 371 (c)(1),
(2), (4) Date: Jun. 8, 2012

(87) PCT Pub. No.: WO2011/070168
PCT Pub. Date: Jun. 16, 2011

(65) Prior Publication Data
US 2012/0237627 A1    Sep. 20, 2012

(30) Foreign Application Priority Data

Dec. 11, 2009  (BE) .................................. 2009/0780

(51) Int. Cl.
*A01N 65/00*    (2009.01)
(52) U.S. Cl.
USPC ........................................................ 424/725

(58) Field of Classification Search
None
See application file for complete search history.

(56) References Cited

U.S. PATENT DOCUMENTS

| 6,027,716 A | 2/2000 | Levin et al. |
| 6,099,866 A | 8/2000 | Slimak |
| 2008/0031905 A1 | 2/2008 | Cram et al. |

FOREIGN PATENT DOCUMENTS

NL    9101053    1/1993

OTHER PUBLICATIONS

International Search Report for PCT/EP2010/069412, English translation attached to original, Both completed by the European Patent Office on Feb. 24, 2011, All together 5 Pages.

*Primary Examiner* — Michael Meller
(74) *Attorney, Agent, or Firm* — Brooks Kushman P.C.

(57) ABSTRACT

A pharmaceutical composition characterized in that the composition contains at least 4 wt % relative to the total weight of the composition of an active principle selected from among cetearyl octanoate and hexanoic acid, beeswax and optionally one or more pharmaceutically acceptable excipient(s), as well as to the use thereof for the treatment of cutaneous pre-burns or burns and for reducing pain following a thermal shock.

8 Claims, 1 Drawing Sheet

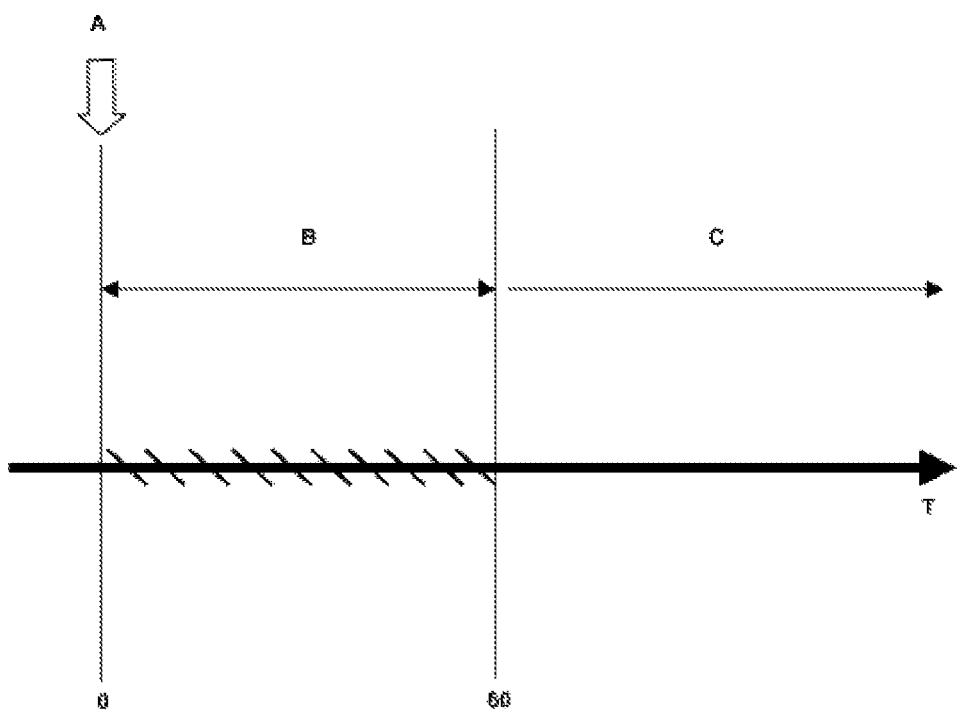

PHARMACEUTICAL COMPOSITION FOR TREATING CUTANEOUS BURNS

CROSS-REFERENCE TO RELATED APPLICATION

This application is the U.S. national phase of PCT Appln. No. PCT/EP2010/069412 filed on Dec. 10, 2010, which claims priority to BE Patent Application No. 2009/0780 filed on Dec. 11, 2009, the disclosures of which are incorporated in their entirety by reference herein.

TECHNICAL FIELD

The present invention relates to the field of pharmaceutical compositions that are of use for treating cutaneous injuries and contractions caused by thermal burns, and also to the use thereof and the associated therapeutic treatment methods.

PRIOR ART

The cutaneous burn, outside the case of a chemical burn, can be defined as a thermal attack on the skin. A cutaneous burn can lead to partial or total destruction of the skin, of the soft tissues, of the ears and eyes, of the head hair and body hair, of the nails and even of the bones. Most burns affect only the skin, namely: the epidermis and the dermis. Several factors are taken into account for evaluating the seriousness of a burn, namely: the surface area affected, the depth, the localization and also the cause of the burn.

Cutaneous burns are usually listed according to their degrees of seriousness. A first-degree burn is generally limited to an erythema, and affects only the surface layers of the epidermis. A second-degree burn "A" affects the epidermis and also a part of the dermis. These burns manifest themselves through the appearance of erythema and also of phlyctenae at the surface thereof. This type of burn may be responsible for more or less acute pain depending on the degree to which the nerves are affected. The rupturing of blood capillaries may already be associated therewith. A deep second-degree burn "B" can extend beyond the dermis and reach the subcutaneous soft tissues. A third-degree burn causes total destruction or vitrification of the epidermis and of the dermis. This type of burn often damages the subcutaneous tissues such as the vascular tissue, the muscles and the nerves. In order to treat this type of burn, it is customary practice to perform skin grafts since no epidermal cicatrization is theoretically possible. The fourth-degree burn affects the muscles and can even extend to the bones. In this case, the appearance of the skin is said to be "carbonized" and the recommended treatment may be amputation. In this case, the patient's vital prognosis is then often involved depending on the age of the patient and the surface area affected.

Burns can be caused by various causes, such as:
contact with a solid, liquid or gaseous heat source (thermal burn),
radiation from a heat source (thermal burn),
certain medical treatments such as radiotherapy,
contact with cold (frostbite),
an electrocution (electrical burn),
contact with a chemical product (chemical burn),
friction (friction burn which is generally likened to a thermal burn).

According to the World Health Organization, burns are responsible for more than 300 000 deaths annually throughout the world (outside cases of war). In France, in 2005, the Direction Générale de l'Offre de Soins (DGOS) [Directorate General for Care Provision] listed more than 400 000 cases of burns having required medical care, 70% of which appear to be linked to a domestic accident. Burns requiring comfort treatment could involve 10% of the population. There is therefore a real need to propose pharmaceutical compositions for treating cutaneous burns.

Pharmaceutical compositions intended for treating burns are already known. For example, document NL9101053 describes an oil-in-water emulsion forming a continuous film which is almost insoluble and impermeable. This oil-in-water emulsion also contains cetearyl stearate and is of use for treating irritated skin and healed burns.

Nevertheless, it is generally observed that the time for total healing of a first-degree or second-degree cutaneous burn can be up to two weeks.

It therefore appears necessary to propose alternative pharmaceutical compositions and also therapeutic treatment methods for treating cutaneous burns.

GENERAL DESCRIPTION OF THE INVENTION

The present invention relates to a pharmaceutical composition comprising at least 4% by weight, relative to the total weight of the composition, of an active ingredient chosen from cetearyl octanoate and/or hexanoic acid, in combination with beeswax and, optionally, one or more pharmaceutically acceptable excipient(s).

The research carried out in the context of the present invention has made it possible to demonstrate that, during the burn formation process, several stages can be identified:
1) contact with the cause of the burn (also called heat impact),
2) beginning of deformation (or modification) of the epidermis and then of the dermis, of the subcutaneous soft tissues and, possibly, of the vascular tissue or even of the organs; this deformation can be likened to a shrinking or contraction of the tissues,
3) continued radiation of the heat and continued deformation of the various local or neighboring tissues in parallel with evaporation of the water contained in the tissues,
4) stabilization of the tissue necroses and deformations (stabilized cutaneous burns can take several months for serious cases).

In view of this, it appears surprising that the pharmaceutical compositions already known appear to treat only the cutaneous injuries brought about by a burn after stabilization of the tissue necroses and deformations (stage 4). One of the reasons is certainly that the physician is seen during the stabilization phase (stage 4) and not during the dynamics of the internal transformation of the tissues (stages 2 and 3).

Nevertheless, it therefore appears to be possible to envision intervening at various stages of the burn formation process (for example, at stages 2, 3 and/or 4). One of the merits of the invention is to have made it possible to identify a particular state during the cutaneous burn formation process, namely the pre-burn state corresponding to stages 2 and 3 previously described. For the purpose of the present invention, the term "pre-burn" denotes the cutaneous injuries corresponding to the deformation of the epidermis, of the dermis and of the tissues associated with evaporation of the water that is contained therein, and which are brought about within a period of generally less than or equal to 60 seconds and in particular within a period of less than or equal to 45 seconds starting from the contact with the cause of the burn.

Consequently, the pharmaceutical composition according to the present invention proposes to treat the cutaneous injuries and deformations when it is still a question of pre-burns (stages 2 and 3 previously defined). Another merit of the invention is to have demonstrated that treatment of the cutaneous injuries and deformations at the pre-burn stage enables faster complete healing since it occurs before stabilization. It is believed that this healing is 300% to 500% faster in most cases.

Furthermore, it has been demonstrated that the pharmaceutical composition according to the present invention is not only effective for treating stabilized cutaneous burns (stage 4), by internal provision of certain lipid components, but also and especially for treating pre-burns (stages 2 and 3).

Surprisingly, it has been noted that the use of the pharmaceutical composition according to the present invention makes it possible to much reduce the total healing time of a cutaneous burn or pre-burn.

Without wishing to be bound by any theory, it would appear that the dehydration caused by the impact of the heat source is immediately compensated for by the application of the pharmaceutical composition according to the invention. The composition according to the invention allows immediate hydration of the area affected in order to restore the evaporated water in the cells and thus to limit the afflux of blood or of physiological fluid in the area affected. In this way, erythema or phlyctena formation is considerably limited. Furthermore, this rapid rehydration of the tissues would thus make it possible to reduce necrosis thereof or deterioration thereof. It would also appear that the higher temperature exhibited by the cutaneous injuries observed at the pre-burn stage compared with the normal body temperature allows better penetration of the pharmaceutical composition. Thus, the time for total healing of a burn is significantly reduced. In addition, this total and rapid healing makes it possible to avoid the problems associated with the risk of infection with microorganisms that often appear after 7 days, depending on the condition of the local blood stream. In addition, since the nerve endings are less compressed, the pain felt is reduced. In non-serious cases, it disappears after 10 minutes owing to the non-compression of the nerves by the shrunken tissues. The use of the pharmaceutical composition of the present invention therefore makes it possible to reduce the cutaneous after-effects that prevent use of the burnt limb and require treatment in order to prevent infections. Furthermore, the use of the composition according to the present invention also makes it possible to reduce scarring which usually remains visible for several months.

Surprisingly, it has been observed that the pharmaceutical composition according to the present invention exhibits a rapid cutaneous penetration.

A subject of the invention also relates to the use of the pharmaceutical composition according to the present invention for treating cutaneous burns and in particular for treating cutaneous pre-burns.

Another subject of the present invention relates to a therapeutic method, characterized in that said pharmaceutical composition is brought into contact with the cutaneous burn and in particular on a cutaneous pre-burn.

DESCRIPTION OF THE DRAWING

FIG. 1: scheme illustrating the mode of action of the pharmaceutical composition according to the invention. (T) represents the axis of the time in seconds. (A) represents the contact with the cause of heat (or heat impact). (B) corresponds to the cutaneous pre-burn period during which the composition according to the invention preferentially acts and which is between 0 and 60 seconds. (C) corresponds to the period of stabilization of tissue necroses and deformations (stabilized burns).

DETAILED DESCRIPTION OF THE INVENTION

The present invention relates to a pharmaceutical composition characterized in that it comprises at least 4% by weight, relative to the total weight of the composition, of an active ingredient chosen from cetearyl octanoate or hexanoic acid or a combination of both, in combination with beeswax and, optionally, one or more pharmaceutically acceptable excipient(s).

According to the present invention, the term "cetearyl octanoate" denotes an octanoic ester of cetyl alcohol and of stearyl alcohol of empirical formula $C_{24}H_{48}O_2$.

According to the present invention, the term "hexanoic acid" denotes the compound of general formula $C_6H_{12}O_2$.

According to the present invention, the term "beeswax" denotes beeswax of natural origin or synthetic beeswax (CAS 71243-51-1) or white beeswax.

In the present invention, the term "pharmaceutically acceptable" is intended to denote what is of use in the preparation of a pharmaceutical composition, that is generally safe, nontoxic and neither biologically undesirable nor otherwise undesirable and that is acceptable for a therapeutic use, in particular by topical application.

Advantageously, the pharmaceutical composition according to the invention comprises between 4 and 15% by weight of active ingredient relative to the total weight of the composition. According to one embodiment of the invention, the pharmaceutical composition contains at least 4%, preferably at least 5%, preferably at least 6.5%, preferably at least 8%, preferably at least 10%, preferably at least 12% and even more preferably at least 14.5% by weight of active ingredient relative to the total weight of the composition. According to another embodiment of the invention, the pharmaceutical composition contains at most 15%, preferably at most 12%, preferably at most 10%, preferably at most 8%, preferably at most 6.5% and preferably at most 5% by weight of active ingredient relative to the total weight of the composition. Preferentially, the pharmaceutical composition comprises between 4 and 12%, preferably between 5 and 10% and preferably between 6.5 and 8% by weight of active ingredient relative to the total weight of the composition.

Preferably, the pharmaceutical composition comprises between 2 and 5% by weight of beeswax relative to the total weight of the pharmaceutical composition. According to one embodiment of the invention, the pharmaceutical composition comprises at least 2%, preferably at least 2.2%, preferably at least 2.5%, preferably at least 3%, preferably at least 3.5%, and according to one embodiment at least 4% by weight of beeswax relative to the total weight of the pharmaceutical composition. According to another embodiment of the invention the pharmaceutical composition comprises at most 5%, preferably at most 4%, preferably at most 3%, preferably at least 2.5% and preferably at least 2.2% by weight of beeswax relative to the total weight of the pharmaceutical composition. Advantageously, the pharmaceutical composition comprises between 2 and 5% and preferably between 2 and 4% by weight of beeswax relative to the total weight of the present invention.

Advantageously, the ratio of the active ingredient to the beeswax is between 0.8 and 7.5. According to one embodiment, said ratio is between 1.5 and 5 and is preferably between 2 and 4.

According to one embodiment of the invention, the active ingredient of the pharmaceutical composition is cetearyl octanoate.

In addition, the pharmaceutical composition may also contain one or more additional additive(s) chosen from dexpanthenol (vitamin B5) and/or polydimethylsiloxane (dimethicone) with the aim in particular of increasing, inter alia, the moisturizing properties of the pharmaceutical composition.

According to one embodiment of the invention, the pharmaceutical composition may also comprise dexpanthenol. Preferably, the pharmaceutical composition comprises between 0.1 and 5% by weight of dexpanthenol relative to the total weight of the composition. According to one embodiment of the invention, the pharmaceutical composition comprises at least 0.1%, preferably at least 0.2%, preferably at least 0.3%, preferably at least 0.4%, preferably at least 1%, preferably at least 2%, preferably at least 3%, preferably at least 4% and preferably at least 4.5% by weight of dexpanthenol relative to the total weight of the composition. According to another embodiment of the invention, the pharmaceutical composition comprises at most 5%, preferably at most 4%, preferably at most 3%, preferably at most 2%, preferably at most 0.4%, preferably at most 0.3% and preferably at most 0.2% by weight of dexpanthenol relative to the total weight of the composition. Advantageously, the pharmaceutical composition comprises between 0.2% and 3% by weight of dexpanthenol relative to the total weight of the composition.

According to one embodiment of the invention, the pharmaceutical composition may also comprise polydimethylsiloxane (dimethicone). Preferably, the pharmaceutical composition comprises between 2 and 5% by weight of polydimethylsiloxane relative to the total weight of the pharmaceutical composition. According to one embodiment of the invention, the pharmaceutical composition comprises at least 2%, preferably at least 2.2%, preferably at least 2.5%, preferably at least 3%, preferably at least 4%, and according to one embodiment at least 4.5% by weight of polydimethylsiloxane relative to the total weight of the pharmaceutical composition. According to another embodiment of the invention, the pharmaceutical composition comprises at most 5%, preferably at most 4%, preferably at most 3%, preferably at most 2.5% and preferably at most 2.2% by weight of polydimethylsiloxane relative to the total weight of the pharmaceutical composition. Advantageously, the pharmaceutical composition comprises between 2 and 4% and preferably between 2 and 3% by weight of polydimethylsiloxane relative to the total weight of the present invention.

According to one embodiment of the invention, the pharmaceutical composition comprises cetearyl octanoate, beeswax, dexpanthenol and polydimethylsiloxane.

The pharmaceutical composition may also comprise one or more essential oil(s) or derivatives thereof, for example with disinfecting properties in order to prevent any possible infection of bacterial or fungal origin, or with skin soothing and moisturizing properties. The essential oils may optionally be refined. The derivatives of essential oil(s) are, for example, glycolic extracts, tinctures or macerated products of essential oil(s). This or these essential oil(s) or a derivative thereof may be selected from the group consisting of: *Melaleuca alterniflora* essential oil or a derivative thereof, Tepezcohuite essential oil or a derivative thereof, eucalyptus essential oil or a derivative thereof, thyme essential oil or a derivative thereof, rosemary essential oil or a derivative thereof, lemon essential oil or a derivative thereof, clover essential oil or a derivative thereof, cinnamon essential oil or a derivative thereof, pine essential oil or a derivative thereof, lavender essential oil or a derivative thereof, *Cistus ladaniferus* essential oil or a derivative thereof, St John's Wort essential oil or a derivative thereof and musk rose essential oil or a derivative thereof.

Preferably, the essential oil(s) or a derivative thereof will be selected from the group consisting of *Melaleuca alterniflora* essential oil or a derivative thereof, Tepezcohuite essential oil or a derivative thereof, St John's Wort essential oil or a derivative thereof and musk rose essential oil or a derivative thereof.

With regard to the derivative of essential oil(s), mention may in particular be made of the glycolic extract or the tincture or the macerated product of Tepezcohuite. Mention may also be made of the glycolic extract or the tincture or the macerated product of St John's Wort.

According to one embodiment of the invention, the pharmaceutical composition comprises between 0.01% and 10% by weight of essential oil(s) or a derivative thereof, relative to the total weight of the composition, and preferably between 0.1% and 5% by weight of essential oil(s) or a derivative thereof, relative to the total weight of the composition.

The pharmaceutical composition may also contain one or more local anesthetic(s) chosen from the following group: lidocaine, prilocaine, scandicaine, etidocaine, bupivacaine, ropivacaine, levobupivacaine, articaine and mepivacaine. According to one embodiment of the invention, it will be lidocaine. Preferably, the pharmaceutical composition comprises between 10 and 20% by weight of local anesthetic(s) relative to the total weight of the pharmaceutical composition. According to one embodiment, the pharmaceutical composition comprises at least 10% and preferably at least 15% and preferably at least 18% by weight of local anesthetic(s) relative to the total weight of the pharmaceutical composition. According to another embodiment, the pharmaceutical composition comprises at most 20%, preferably at most 15% and preferably at most 12% by weight of local anesthetic(s) relative to the total weight of the pharmaceutical composition. Advantageously, the pharmaceutical composition comprises between 10 and 15% by weight of local anesthetic(s) relative to the total weight of the pharmaceutical composition.

According to one embodiment, the pharmaceutical composition may also comprise allantoin.

The pharmaceutical composition may be in the forms which are usually known for topical administration, i.e. in particular, lotions, foams, gels, dispersions, water-in-oil or oil-in-water or multiple emulsions, sprays, sera, masks, body milks or creams, with excipients that allow in particular cutaneous penetration in order to improve the properties and the accessibility of the active ingredients. The pharmaceutical composition may be in the forms which are usually known for administration by injection. The term "injection" is intended to mean a subcutaneous or intradermal administration. In this case, the pharmaceutical composition is in an injectable form incorporated, for example, into a sterile syringe. The syringe may, for example, be sterilized by treatment with beta- or gamma-rays.

Advantageously, the pharmaceutical composition is a water-in-oil emulsion or an oil-in-water emulsion.

The pharmaceutical composition may also comprise excipients normally used in the field of pharmaceutical compositions intended to be applied topically (for example, dermatological compositions) or by injection.

The fatty phase of the present pharmaceutical composition may also comprise lipophilic compounds such as oils, gums, pastes and waxes.

The oils are preferably chosen from plant oils, animal oils, mineral oils, synthetic oils, silicone oils, liquid fatty acid esters, liquid fatty acids and liquid fatty amides.

As plant oil, mention may in particular be made of sweet almond (*Prunus amygdalus dulcis*) oil, avocado oil, castor oil, olive oil, jojoba liquid wax, sunflower oil, wheat germ oil, sesame oil, groundnut oil, grapeseed oil, soyabean oil, rapeseed oil, safflower oil, coconut oil, corn oil, hazelnut oil, apricot kernel oil and beauty-leaf oil.

As animal oil, mention may in particular be made of perhydrosqualene.

As synthetic oil, mention may be made of squalane, poly (α-olefin)s such as isododecane or isohexadecane, transesterified plant oils and fluoro oils.

As silicone oils, mention may be made of cyclic polydimethylsiloxanes (for example: cyclomethicone or dimethicone), such as decamethylpentasiloxane and low-viscosity linear polymethylsiloxanes (150 to 500 cst).

In addition to the beeswax used in the pharmaceutical composition may optionally contain the waxes that can be used are, for example, waxes of animal, plant, mineral or synthetic origin, such as fluoro or perfluoro waxes, lanolin waxes, Candellila, cocoa butter and shea butter waxes, fur tree wax, cotton wax; microcrystalline waxes, paraffin wax, petrolatum, petroleum jelly, ozokerite; hydrogenated oils with a melting point of greater than 40° C., such as hydrogenated jojoba oil, and polyethylene waxes.

The pharmaceutical composition may also contain emulsifiers normally used. The emulsifying system may comprise in particular one or more compounds chosen from ethoxylated fatty alcohols, esters of fatty acids and of PEG, ethoxylated fatty acid partial glycerides, polyglycerolated fatty acid triglycerides and ethoxylated derivatives thereof. Suitable ethoxylated fatty alcohols that may be mentioned are products of addition of ethylene oxide with behenyl alcohol, in particular those comprising from 6 to 12 oxyethylene groups (for example, Beheneth-9 or Beheneth-10); products of addition of ethylene oxide with stearyl alcohol, in particular those comprising 6 to 12 oxyethylene groups (for example, steareth-9); products of addition of ethylene oxide with isostearyl alcohol, for example those comprising 6 to 12 oxyethylene groups (isosteareth-9), and mixtures thereof.

The pharmaceutical composition may comprise nonionic surfactants, oxyethylenated fatty alcohols different than those previously described, namely the products of addition of ethylene oxide with lauryl alcohol (laureth-9 to laureth-50); the products of addition of ethylene oxide with cetearyl or cetylstearyl alcohol (ceteareth-9 to ceteareth-30), the products of addition of ethylene oxide with cetyl alcohol (ceteth-9 to ceteth-30); and mixtures thereof.

Additional surfactants may optionally be included in the composition. These additional surfactants may be the salts of a fatty acid having 8 to 30 carbon atoms, for instance the salts of palmitic acid, stearic acid or behenic acid, fatty esters of glycerol, for instance glyceryl stearate; oxyethylenated derivatives of the fatty acid salts and of the fatty esters of glycerol, comprising 2 to 8 ethylene oxide groups, and mixtures thereof.

The pharmaceutical composition may also comprise preservatives normally used in the field of pharmaceutical compositions. They may in particular be antimicrobial agents such as preservatives or antifungal agents chosen from alcohols, which may contain one or more aromatic substituents, for example phenoxyethanols such as 2-phenoxyethanol or 1-phenoxy-2-propanol, benzyl alcohol, 2-hydroxybiphenyl, parabens, such as methylparaben, ethylparaben, propylparaben, butylparaben, isobutylparaben, sodium methylparaben, sodium ethylparaben, sodium propylparaben, sodium butylparaben or sodium isobutylparaben, ethyl, butyl, propyl or methyl para-hydroxybenzoate, imidazolidinyl urea, diazolidinyl urea, sodium hydroxymethylglycinate, halogenated derivatives such as iodopropynyl butylcarbamate, 2-bromo-2-nitropropane-1,3-diol, 2,4,4'-trichloro-2'-hydroxydiphenyl ether (triclosan), 3,4,4'-trichlorocarbanilide (triclocarban), chlorbutanulum, 2,4-dichlorobenzyl alcohol, N-(4-chlorophenyl)-N'-(3,4-dichlorophenyl) urea, 1,2-dibromo-2,4-dicyanobutane, chloroxylenol, ketoconazole, oxiconazole, butoconazole, clotrimazole, econazole, enilconazole, fenticonazole, miconazole, sulconazole, tioconazole, fluconazole, itraconazole, terconazole, active agents containing one or more cationic nitrogens, such as cetyltrimethylammonium chloride, cetylpyridinium chloride, benzethonium chloride or benzalkonium chloride, optionally in combination with a perborate-stabilized hydrogen peroxide, diisobutylethoxyethyl-dimethylbenzylammonium chloride, diisobutylphenoxyethoxyethyldimethylbenzylammonium chloride, N-alkyl-N,N-dimethylbenzylammonium chloride, bromide or saccharinate, trimethylammonium chloride, sodium aluminum chlorohydroxy acetate, tricetylmethylammonium chloride, diaminoalkylamide, organic acids and their salts, such as citric acid, unsaturated antimicrobial agents such as farnesol, terbinafine or naftifine, heterocyclic aromatic agents such as bifonazole, cloconazole or isoconazole, any other antimicrobial or antifungal agent known to those skilled in the art; and mixtures thereof.

In addition, the pharmaceutical composition may also comprise acids and bases for adjusting the pH range of said pharmaceutical composition. The bases may be inorganic (sodium hydroxide, potassium hydroxide, aqueous ammonia) or organic, such as mono-, di- or triethanolamine, an aminomethylpropanediol, N-methylglucamine, basic amino acids such as arginine and lysine; and mixtures thereof.

The present invention also relates to the use of a pharmaceutical composition as defined above, for treating cutaneous burns and in particular for treating cutaneous pre-burns.

The pharmaceutical composition according to the present invention is of use for treating cutaneous pre-burns or burns of different origin, namely: cutaneous pre-burns or burns caused by contact with or radiation from a hot source, cutaneous pre-burns or burns caused by medical treatments such as radiotherapy, cutaneous pre-burns or burns caused by contact with cold, cutaneous pre-burns or burns caused by friction, and also cutaneous pre-burns or burns caused by short-lived exposure to sunlight. Advantageously, the pharmaceutical composition according to the invention is in particular of use for treating cutaneous pre-burns or burns caused by contact with or radiation from a hot source, caused by medical treatments such as radiotherapy or caused by friction. According to another aspect of the invention, the pharmaceutical composition may be of use for treating pre-burns or burns of the mucus membranes (for example, the walls of the digestive system, such as the esophagus or the lips, the urogenital regions, etc.). The pharmaceutical composition according to the invention is of use for treating first-degree, second-degree or third-degree pre-burns or burns.

According to one aspect of the invention, the use is characterized in that the pharmaceutical composition is brought into contact with the cutaneous injuries within a period of less than or equal to 60 seconds starting from the contact with the cause of the pre-burn or burn in the case of a topical administration, or within a period of less than or equal to 30 minutes starting from the contact with the cause of the pre-burn or burn in the case of an administration by injection.

Preferably, the use is characterized in that the pharmaceutical composition is brought into contact with the cutaneous injuries within a period of less than or equal to 45 seconds starting from the contact with the cause of the pre-burn or burn in the case of a topical administration.

According to one embodiment of the invention, the use is characterized in that the pharmaceutical composition is brought into contact with the cutaneous injuries within a period of less than or equal to 25 minutes starting from the contact with the cause of the pre-burn or burn in the case of an administration by injection.

According to one embodiment of the invention, the use of the pharmaceutical composition is characterized in that the pharmaceutical composition is administered 30 times subsequently during 60 minutes, or 20 times during 60 minutes, or 10 times during 30 minutes, or 5 times during 15 minutes.

The present invention also relates to a therapeutic treatment method characterized in that the pharmaceutical composition according to the present invention is brought into contact with a cutaneous burn and in particular with a cutaneous pre-burn.

Advantageously, the therapeutic treatment method is characterized in that the pharmaceutical composition is brought into contact with the cutaneous injuries within a period of less than or equal to 60 seconds starting from the contact with the cause of the cutaneous pre-burn or burn in the case of a topical administration, or within a period of less than or equal to 30 minutes in the case of an administration by injection.

Preferably, the therapeutic treatment method according to the present invention is characterized in that the pharmaceutical composition is brought into contact with the cutaneous injuries within a period of less than or equal to 45 seconds starting from the contact with the cause of the cutaneous pre-burn or burn in the case of a topical administration.

According to one embodiment, the therapeutic treatment method according to the present invention is characterized in that the pharmaceutical composition is brought into contact with the cutaneous injuries within a period of less than or equal to 25 minutes starting from the contact with the cause of the cutaneous pre-burn or burn in the case of an administration by injection.

The present invention also relates to a therapeutic treatment method for reducing the intensity of pain caused by a thermal shock, characterized in that the pharmaceutical composition is brought into contact with the cutaneous injuries within a period of less than or equal to 60 seconds starting from the contact with the cause of the cutaneous pre-burn or burn in the case of a topical administration, or within a period of less than or equal to 30 minutes in the case of an administration by injection.

Example 1

Clinical Trials a) Clinical Trial Protocol

The pharmaceutical composition according to the invention was tested on several patients with pre-burns of different origin and different seriousness. For each of the following cases, the pharmaceutical composition was applied directly to the cutaneous pre-burn within a period of 45 seconds starting from the contact with the cause of the burn, and then regularly during a defined period.

b) Results of the Clinical Trials

Patient 1: This patient exhibited a second-degree pre-burn, the origin of which came from direct contact of the arm with an oven heating element heated to 350° C. The pharmaceutical composition according to the invention was applied within a period of 45 seconds starting from the contact with the oven heating element heated to 350° C., and it was then applied every 3 minutes during 15 minutes and then regularly during two days. At the end of this period, any visible trace of the cutaneous injuries had disappeared: the area of the skin affected did not show any erythema or phlyctenae, and was not detached. The pain disappeared after 3 hours.

Patient 2: This patient exhibited a second-degree pre-burn caused by contact of the palm of the hand with a red-hot drill bit at 400° C. The pharmaceutical composition according to the invention was applied within a period of 45 seconds starting from the contact with the red-hot drill bit, and it was then applied regularly during two days. At the end of this period, any visible trace of the cutaneous injuries had disappeared: the area of the skin affected showed no erythema or phlyctenae and was not detached. The pain disappeared after 2 hours.

Patient 3: This patient exhibited a first-degree pre-burn caused by contact of the hand with steam. The pharmaceutical composition according to the invention was applied within a period of 45 seconds starting from the contact with the steam, and it was then applied regularly during 3 hours. At the end of this period, any visible trace of the cutaneous injuries had disappeared: the area of the skin affected showed no erythema or phlyctenae and was not detached. This case was repeated on 5 other patients. The pain disappeared after 10 minutes.

Patient 4: This patient exhibited a second-degree "A" pre-burn caused by friction from the chain of his thermal chainsaw on his thigh. The pharmaceutical composition according to the invention was applied within a period of 45 seconds starting from the contact with the chainsaw chain, and it was then applied regularly during 3 days. At the end of this period, any visible trace of the cutaneous injuries had disappeared: the area of the skin affected showed no erythema or phlyctenae and was not detached. The pain disappeared after 10 hours.

Patient 5: This patient exhibited a second-degree "B" pre-burn caused by contact of a motorcycle exhaust pipe on the leg. The pharmaceutical composition according to the invention was applied within a period of 45 seconds starting from the contact with the motorcycle exhaust pipe, and it was then applied regularly during 3 days. At the end of 5 days, any visible trace of the cutaneous injuries had disappeared: the area of the skin affected showed no erythema or phlyctenae and was not detached. The pain disappeared after 24 hours.

These results demonstrate that the pharmaceutical composition according to the invention is particularly effective for treating cutaneous pre-burns and significantly reducing the cutaneous injuries that they cause. Although it is usually observed that the time necessary for the cutaneous injuries caused by a second-degree burn to disappear is approximately two weeks, in the case of the use of the pharmaceutical composition according to the invention, this time is reduced to 2 or 3 days. This significant decrease in the healing time also makes it possible to reduce the risk of infection caused by microorganisms (of bacterial or fungal origin) often observed after 7 days in the case of cutaneous injuries caused by a burn. Furthermore, it should be noted that the pain caused by the cutaneous injuries is significantly reduced by using the pharmaceutical composition according to the invention.

Example 2

Pharmaceutical Composition According to the Invention

| % amount | Name | Function |
| --- | --- | --- |
| q.s. 100% | Water | Moisturization |
| 5-9% | Fatty phase and surfactants | Emulsifiers |
| 2-5% | Polydimethylsiloxane | Moisturization |
| 2-5% | Beeswax | Nourishing and soothing agent |
| 4-15% | Cetearyl ethylhexanoate | Active ingredient |
| 3-5% | Sorbitol | Aqueous phase agent |
| 0.1-5% | Dexpanthenol | Moisturization |
| 1-1.5% | Cetyl alcohol | Emulsifier |
| 0.15-0.35% | Carbomer | Viscosity modifier |
| 0.4-3% | *Melaleuca alterniflora* essential oil | Disinfectant |
| 0.1-0.9% | Essential oils and macerated products | Soothing agent |
| 0.15% | Parabens or the like | Preservatives |

The invention claimed is:

1. A method for treating pre-burns or burns on a human consisting essentially of contacting a cutaneous pre-burn or a burn with therapeutically effective amounts of a composition consisting essentially of water, beeswax, one or more essential oils selected from the group consisting of St. John's wort essential oil, *Melaleuca alterniflora* essential oil, and musk rose essential oil; a first compound selected from the group consisting of polydimethylsiloxane, dexpanthenol, and combinations thereof; and a second compound selected from cetearyl octanoate, cetearyl ethyl hexanoate, and hexanoic acid.

2. The method of claim 1, wherein the composition is brought into contact with the cutaneous pre-burn or burn within a period of less than or equal to 60 seconds starting from when the cutaneous pre-burn or burn occurs for administration topically or within a period of less than or equal to 30 for administration by injection.

3. The method of claim 1, wherein the composition is brought into contact with the cutaneous pre-burn or burn within a period of less than or equal to 45 seconds starting from when the cutaneous pre-burn occurs for administration topically.

4. The method of claim 1, wherein the composition is brought into contact with the cutaneous pre-burn or burn within a period of less than or equal to 25 minutes starting from when the cutaneous pre-burn occurs for administration by injection.

5. The method of claim 1 wherein the compound is administered topically or by injection.

6. The method of claim 1, wherein beeswax is present in an amount of 2 to 5% by weight relative to the total weight of the composition.

7. The method of claim 1, wherein the composition is in a water-in-oil emulsion or an oil-in-water emulsion.

8. A method for treating pre-burns or burns on a human consisting essentially of contacting a cutaneous pre-burn or a burn with therapeutically effective amounts of a composition consisting essentially of water, beeswax, one or more essential oils selected from the group consisting of St. John's wort essential oil, Tepezcohuite essential oil, eucalyptus essential oil, thyme essential oil, rosemary essential oil, lemon essential oil, clover essential oil, cinnamon essential oil, pine essential oil, lavender essential oil, *Cistus ladaniferus* essential oil, and musk rose essential oil, and combinations thereof; a first compound selected from the group consisting of polydimethylsiloxane, dexpanthenol, and combinations thereof; a second compound selected from Cetearyl octanoate, cetearyl ethyl hexanoate, and hexanoic acid; and a third compound selected from the group consisting of lidocaine, prilocaine, scandicaine, etidocaine, bupivacaine, ropivacaine, levobupivacaine, articaine and mepivacaine.

\* \* \* \* \*

UNITED STATES PATENT AND TRADEMARK OFFICE
CERTIFICATE OF CORRECTION

| | | |
|---|---|---|
| PATENT NO. | : 8,597,696 B2 | Page 1 of 1 |
| APPLICATION NO. | : 13/514625 | |
| DATED | : December 3, 2013 | |
| INVENTOR(S) | : Jean-Jacques Debetencourt | |

It is certified that error appears in the above-identified patent and that said Letters Patent is hereby corrected as shown below:

In the Claims

Column 12, Line 2, Claim 2:

After "a period of less than or equal to 30"
Insert -- minutes --.

Signed and Sealed this
Thirteenth Day of May, 2014

Michelle K. Lee
*Deputy Director of the United States Patent and Trademark Office*